United States Patent [19]

Jaeger

[11] Patent Number: 4,475,410

[45] Date of Patent: Oct. 9, 1984

[54] SAMPLER FOR VISCOUS MATERIALS

[76] Inventor: Ben E. Jaeger, Rte. 2 Box 49, Plano, Ill. 60545

[21] Appl. No.: 444,719

[22] Filed: Nov. 26, 1982

[51] Int. Cl.³ .......................... G01N 1/10; G01N 1/20
[52] U.S. Cl. ................................ 73/863.84; 73/864.34
[58] Field of Search ............ 73/863.84, 863.83, 864.34

[56] References Cited

U.S. PATENT DOCUMENTS

| | | | |
|---|---|---|---|
| 2,794,344 | 6/1957 | Boren | 73/863.84 |
| 2,872,817 | 2/1959 | Pitts | 73/863.84 X |
| 3,681,996 | 8/1972 | Crist | 73/863.73 |
| 3,813,945 | 6/1974 | Crumal | 73/864.34 |
| 4,147,062 | 4/1979 | Jaeger | 73/863.83 |
| 4,262,533 | 4/1981 | Jaeger | 73/863.83 X |
| 4,269,064 | 5/1981 | Johnson et al. | 73/863.84 |

FOREIGN PATENT DOCUMENTS 426165 10/1974 U.S.S.R. .......................... 73/863.83

Primary Examiner—S. Clement Swisher
Assistant Examiner—Tom Noland
Attorney, Agent, or Firm—Gary, Juettner & Pyle

[57] ABSTRACT

A sampler for communicating with the interior of a vessel containing a relatively viscous liquid under pressure extracts a liquid sample of predetermined volumetric displacement from the vessel and conveys the same to a point of collection. The sampler includes a body having a bore in communication with the interior of the vessel, a plunger reciprocable within the bore and a slider reciprocable within the bore rearwardly of the plunger. To obtain a liquid sample, the plunger is moved at least partially into the vessel to establish a sample chamber between the slider and plunger into which liquid flows. The plunger is then moved back into the bore with the sample captured between the plunger and slider until the sample is exposed to a discharge port in the bore, at which point further rearward movement of the sleeve is inhibited, so that continued rearward movement of the plunger forces the liquid out of the sample chamber and through the port.

11 Claims, 2 Drawing Figures

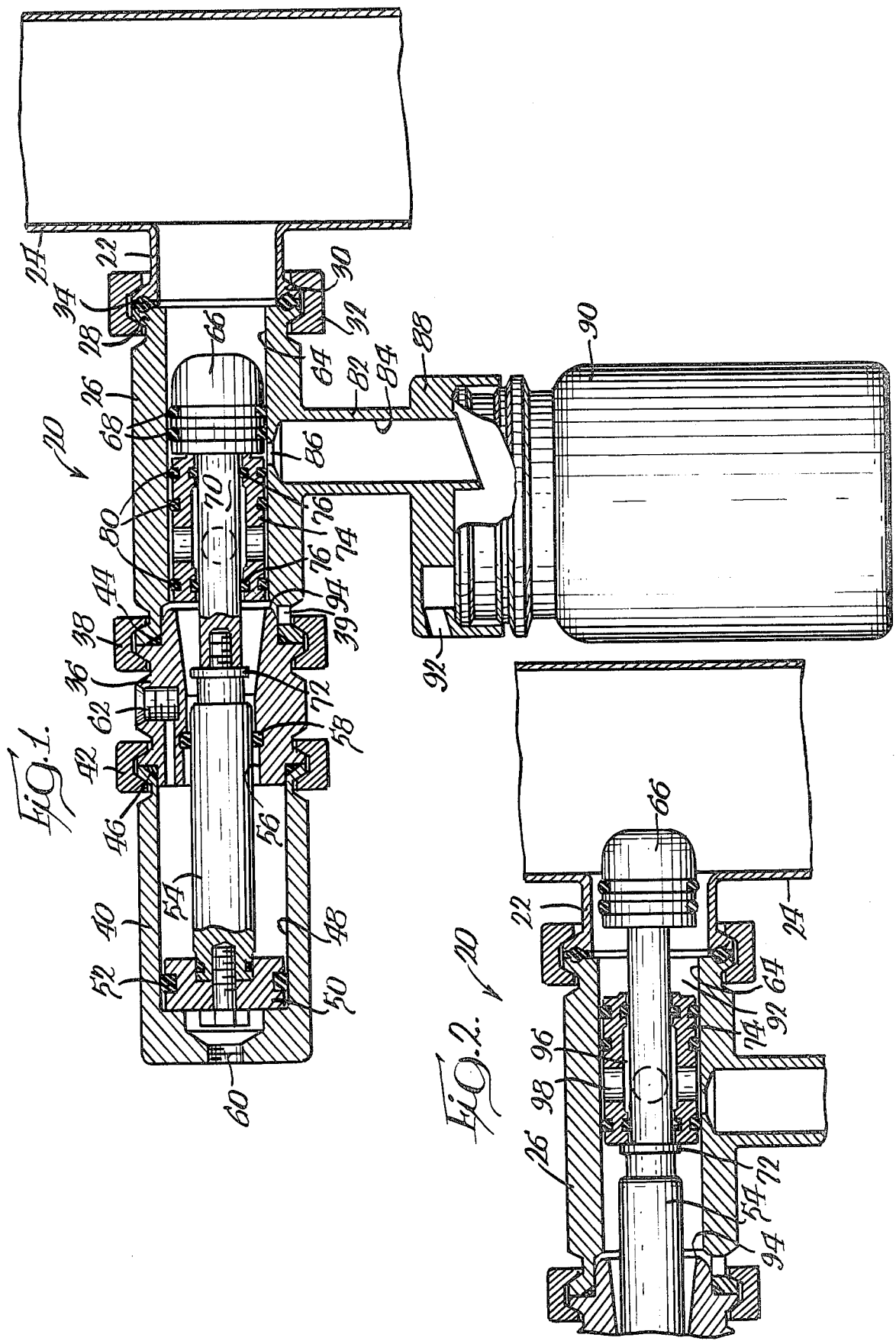

SAMPLER FOR VISCOUS MATERIALS

BACKGROUND OF THE INVENTION

The present invention relates to apparatus for extracting samples of liquid from flow lines or tanks, and in particular to an apparatus for extracting samples of a relatively viscous liquid from a flow line or tank in which the liquid is maintained under pressure.

Various manufacturing operations require that the immediate or overall composition of a liquid flowing through a pipe or conduit be monitored. Such monitoring ordinarily is accomplished with apparatus denoted as samplers, which take samples of liquid from the main body thereof. Where a composite sample of the liquid is required, the sampler may be operated to withdraw a series of small, measured amounts of the liquid as it passes a sampling point. The individual samples are collected, and represent a composite of the total volume of liquid.

Other uses for samplers are in on-line analysis applications in which the immediate composition of a liquid must be determined. For this application, the individual samples of liquid are not collected as a composite sample, but instead are separately analyzed.

To obtain the samples, some samplers continuously divert streams of liquid from the flow lines or tanks, and from the diverted streams the samples are removed in various ways. Attempts to withdraw small measured quantities directly from the pipes or tanks, however, have presented many problems not altogether satisfactorily solved. For example, liquid receiving holes or slots in samplers adapted to be extended directly into a pipe often require an orienting mechanism, and the sampled material can build up in such holes and slots and either block the same or contaminate subsequent samples. In addition, conventional samplers are difficult to disassemble for inspection, cleaning and replacement of parts, and excessive leakage and clogging are problems common to many types of samplers.

Heretofore samplers of the general type have been generally used to obtain samples of thin or relatively nonviscous liquids. In recent years, however, a need has arisen to sample liquids which are viscous, for example catsup, mayonnaise, juice concentrate, asphalt and heavy grease. Conventional samplers do not perform satisfactorily when used to sample such highly viscous liquids, since the sampled material is too thick to effectively flow off and out of the sampler for collection.

One technique that has been used under limited circumstances to assist in ejecting viscous liquids from conventional samplers is to introduce air into the sampler to literally blow the sample out of a discharge port. Unfortunately, a difficulty encountered with many materials resides in the need to maintain the samples free from contamination from the time of their extraction and until they are delivered to a point of collection. Thus, the extracted samples cannot always be exposed to atmosphere for the purpose of ejection, since for materials which absorb oxygen the composition of the samples may be altered, and an accurate analysis of the main body of liquid cannot then be obtained.

OBJECTS OF THE INVENTION

An object of the present invention is to provide a sampler for withdrawing small measured quantities of samples of relatively viscous liquids directly from either a pipe or a tank in which the liquids are maintained under pressure.

Another object is to provide such a sampler in which collected samples are protected from contamination during the sampling process.

A further object is to provide such a sampler which cannot become clogged by material to be sampled, which positively expels the sample at the collection point and which is suited for automatic operation at selected intervals.

Yet another object is to provide such a sampler which is self-cleaning in operation and of simple and economical construction.

SUMMARY OF THE INVENTION

In accordance with the present invention, apparatus for obtaining samples of a liquid product from a vessel containing the product comprises a housing having a bore for communication at a forward end with the interior of the vessel, a discharge port in said bore and a plunger in and slidingly sealed with said bore. A slider is in and slidingly sealed with said bore rearwardly of said plunger, and means are provided for reciprocating said plunger and slider in said bore to move the same forwardly to positions whereat said plunger extends into the vessel and said slider is in said bore spaced rearwardly from said plunger to establish a sample chamber between the same for reception of liquid product, and to then move said plunger and slider rearwardly to capture the sampled product between the same within said bore and to convey the sample to said discharge port. In addition, means are included for arresting further rearward movement of said slider when the product sample is at said discharge port, so that continued rearward movement of said plunger then decreases the volumetric capacity of said sample chamber and forces the liquid product sample from said sample chamber and through said discharge port for collection.

The foregoing and other objects, advantages and features of the invention will become apparent upon a consideration of the following detailed description, when taken in conjunction with the accompanying drawings.

BRIEF DESCRIPTION OF THE DRAWINGS

FIG. 1 is a side elevation view, partly in cross section, illustrating the structural details of a preferred embodiment of sampler for obtaining a sample of relatively viscous liquid from a main body thereof in which the liquid is under pressure and for transporting the sample to a point of collection, showing a plunger of the sampler withdrawn to a position whereat the sample is discharged into a container, and FIG. 2 is similar to FIG. 1, and shows the sampler plunger partially extended into the main body of liquid for obtaining a measured sample of the liquid.

DETAILED DESCRIPTION

Referring to the drawings, there is indicated generally at 20 a sampler structured in accordance with a preferred embodiment of the invention. The sampler is adapted for connection with an access line 22 to a conduit 24 in which is conveyed relatively viscous liquid materials under pressure, such materials including, by way of example, catsup, mayonnaise, juice concentrate, asphalt and heavy grease. The sampler has a plunger which is at least partially extendable into the conduit for receiving within a sample chamber a precisely measured amount of the liquid, with the plunger then being retractable to convey the sample to a collection point, and the sampler may be cyclically actuated so that the collected material represents a composite sample of material flowing through the conduit. The plunger may be actuated by pneumatic or electric motor means, and a plurality of seals maintain liquid seals between the interior of the conduit and the collection point and between the collection point and the motor, thereby to protect the collected samples against contamination. As will become apparent, the sample chamber is washed clean by the liquid each time a sample is obtained, whereby the collected samples accurately represent the liquid in the conduit.

More particularly, the outer portion of the sampler 20 includes a body 26 having a flange 28 at its forward end which connects with a flange 30 on the access line 22 by means of a quick release clamp 32, and a seal 34 establishes a fluid tight connection between the flanges. A head 36 connects at its forward end with the rearward end of the body by means of a quick release clamp 38, and a vent 39 through the body, which may be open to atmosphere or connected with a supply of low pressure air, communicates with the interior of the juncture between the body and head. A barrel 40 is connected at its forward end with the rearward end of the head by a quick release clamp 42, and seals 44 and 46 are respectively between the body and head and between the head and barrel.

A motor means for operating the sampler includes the barrel 40 in which is defined a cylinder passage 48. A piston 50 within the passage is slidingly sealed therewith by a seal 52, and a piston rod 54 connected with the piston extends forwardly through a passage 56 in the head and is slidingly sealed therewith by an annular seal 58. To reciprocate the piston rod, an air inlet 60 communicates with the rearward end of the barrel passage and an air inlet 62 in the head communicates with the forward end of the passage. Thus, introduction of air at the inlet 60 moves the piston and piston rod rightwardly (as shown in the drawings), while introduction of air at the inlet 62 moves the piston and piston rod leftwardly.

The sampling portion of the sampler 20 includes the body 26 in which is defined a cylindrical passage 64. A plunger 66 in the passage is slidingly sealed therewith by a pair of annular seals 68, a rod 70 extends between and is connected with a rearward face of the plunger and a forward end of the piston rod 54, and a flange 72 is defined at the forward end of the piston rod.

Disposed about the rod 70 rearwardly of the plunger 66 and forwardly of the flange 72 is a slider or floating sleeve 74. The slider is reciprocable along the rod 70 and seals 76 form a fluid tight connection between the slider and rod. The slider is also reciprocable within the body passage 64 and sealed therewith by three seals 80. The arrangement is such, for a purpose to be described, that the resistance to movement of the slider along the rod as afforded by the seals 76 is less than the resistance to movement of the slider through the passage 64 as afforded by the seals 80.

The remainder of the sampler 20 comprises means for storing collected liquid samples, and to that end a tubular conduit 82 extends downwardly from the body 26. A passage 84 through the conduit communicates with the body passage 64 through a discharge port or orifice 86, and the discharge port has a diameter which is considerably smaller than that of the passage 84. The tubular conduit terminates in a cap or cover 88 which is threadably connectable with a container 90 for receiving successive samples of liquid, and the cover is vented at 92 for connection with a supply of an inert gas or with a bubbler to maintain the integrity of the collected samples.

In operation of the sampler to obtain a sample of liquid flowing through the conduit 24, air is applied at the inlet 60 to drive the piston rod 54 and therefore the rod 70 and plunger 66 forwardly through the body passage 64. In the case where the vent 39 is open to atmosphere, as the plunger starts to move forward, one of two actions will take place. First, the slider or floating sleeve 74 will remain stationary in the body passage until the flange 72 engages its rear face and carries it forward or, secondly, the slider will move forwardly immediately with the plunger until the plunger clears the passage 64 and the front face of the slider is exposed to the pressurized fluid in the conduit, at which time the pressure of the fluid will force the slider backward against the flange. Should the vent be connected with a supply of low pressure air, then the slider will always follow the plunger forwardly as a result of the pressure of air behind it, until the slider is exposed to the pressure of fluid in the conduit and forced back against the flange, it being understood that the pressure of air introduced through the vent is controlled to be less than the pressure of the fluid in the conduit. In any event the result is the same, and when the plunger is fully extended a sample chamber 92 opens up and is defined around the rod between the rear face of the plunger and the front face of the slider. Since it is desirable to sample measured quantities of liquid, the length of the slider and the distance between the flange and the rear face of the plunger are selected so that, when the plunger is extended and the slider engages the flange, a sample chamber of predetermined volumetric capacity is established for a flow therein of liquid in the conduit.

The maximum forward extension of the plunger 66 into the conduit 24 is shown in FIG. 2. Despite the fact that with the plunger extended the sample chamber 92 is not positioned within the main body of the conduit 24, it fills completely with sampled liquid and any air therein is expelled. There are several theories why this happens. First, for the case where the plunger precedes the slider and the slider is carried forward by the flange 72, when the head of the plunger is extended into the conduit, turbulence is created in the liquid flow around the plunger which causes the liquid to enter and rapidly fill the chamber. According to a second theory, and again for the situation where the plunger precedes the slider, upon extension of the plunger head into the flow a positive pressure is generated at the hemisphere of the plunger upstream of the flow for movement of material into the chamber, while due to venturi effect a negative pressure is generated at the hemisphere of the plunger downstream of the flow, which promotes a flow of liquid into and air out of the chamber. On the other hand, should the slider follow the plunger so that there is no air to expel, then the pressurized liquid will simply flow into the sample chamber developed as the slider is forced rearward to against the flange.

After the forward end of the plunger has been momentarily extended into the conduit, air is introduced at the inlet 62 to move the piston 50 and piston rod 54, and therefore the rod 70 and plunger 66, rearwardly. As the plunger moves rearwardly, the pressure of fluid in the conduit 24 maintains the slider 74 against the flange 72 and moves the slider rearwardly into the body passage 64, thereby maintaining a constant volume of the sample chamber 92 and of the liquid sampled until the plunger again seals with the body passage. Then, with continued retraction of the plunger the pressurized, trapped and sampled fluid within the sample chamber continues to move the slider rearwardly until such time as the slider begins to move past the discharge port 86.

As previously mentioned, the three outer slider seals 80 offer considerably more resistance to movement of the slider through the body passage 64 than do the two inner seals 76 to movement of the slider along the rod 70. For relatively slow movement of the plunger, for example one second out and one second in, the resistance offered by the outer seals is such that when the discharge port 84 is exposed, depressurizing the sample chamber, rearward movement of the slider ceases while rearward movement of the plunger continues to force the relatively viscous liquid sample through the port, it being understood that the point at which rearward movement of the slider initially ceases is a function of the viscosity of the sampled fluid and the rate at which the plunger is retracted. When the entirety of the sample has been expelled from the sample chamber and the plunger again engages the slider, the plunger drives the slider rearwardly as it moves to its fully retracted position. For extremely viscous materials or a very rapid retraction rate of the plunger, it is possible that the rearward face of the slider could be driven against a forward face 94 of the head 36 before the liquid sample is fully expelled.

Also as earlier mentioned, the diameter of the discharge port 86 is considerably less than that of the passage 84 through the tubular conduit 82. This relationship increases the velocity of the ejected fluid sample through the passage, reducing its tendency to simply fill up the passage and possibly be sucked back into the sample chamber on the next sampling cycle. On the other hand, introduction of low pressure air at the vent 39 absolutely eliminates the possibility of sucking material back into the sample chamber, since the slider will then follow the plunger forwardly and the sample chamber cannot then open while it is exposed to the discharge port. Another advantage of introducing low pressure air at the vent is that the air acts as a cushion on the rear face of the slider, and softens the impact between the slider and flange as the slider moves rearwardly during filling of the sample chamber.

Another feature of the invention is that with the plunger 66 fully retracted, the axial length of the slider 74 is about 1/16" less than the distance between the plunger rear face and the forward head face 94. This dimensional relationship accomplishes two useful functions. First, if the rear face of the plunger and the front face of the slider were brought firmly together to squeeze from therebetween the viscous liquid sample, the liquid would tend to cause the plunger and slider to stick together, and upon the next sampling cycle the slider might not be moved rearwardly of the plunger to establish the sample chamber. Secondly, the relationship takes into account the fact that sampled material occasionally contains solid contaminants, and should a solid contaminant be caught in the sample chamber, the shorter axial length of the slider prevents it from being forceably impacted against the front face of the head, which is desirable to protect against damage to the sampler, particularly when the same is made of stainless steel. Note also that the rearward seal 80 on the slider always remains rearwardly of the discharge port 86, which ensures that the port is never exposed to air behind the slider and protects the integrity of the collected liquid samples.

A further feature of the sampler is that it may readily be cleaned for sanitation purposes or to remove contaminants. In that connection, the slider 74 has a central enlargement 96 medially of the passage for receiving the rod 70 and is crossbored at 98. Thus, if the slider and plunger 66 are removed from within the body passage 64, as by removing the quick release clamp 38, the center portion of the slider and the outer portions of the slider and plunger can be flushed clean with hot water.

The invention thus provides an improved sampler for relatively viscous materials. The sampler utilizes the natural pressures or forces at work within the main body of sampled material to operate a floating sleeve or slider on the plunger shaft in such manner that a fixed volume of fluid is extracted from a pressurized line and ejected under the simple reciprocating action of a single plunger and cylinder. By virtue of the fact that during a sample recovery cycle rearward movement of the slider is inhibited either by the resistance of its seals or by a fixed stop, even though the sampled material has a very high viscosity, it is forced from the sample chamber merely by continued rearward movement of the plunger. Also, the sample chamber is flushed clean each and every time it is exposed to a fresh flow of product therein, and should it be necessary to thoroughly clean the portion of the sampler exposed to product, for example because of a change in the nature of product being sampled, the sampler may easily be disassembled and flushed clean with water.

While one embodiment of the invention has been described in detail, various modifications and other embodiments thereof may be devised by one skilled in the art without departing from the spirit and scope of the invention, as defined in the appended claims.

What is claimed is:

1. Apparatus for obtaining samples of a liquid product from a vessel containing the product, comprising a housing having a bore for communication at a forward end with the interior of the vessel, said bore being cylindrical and having a rearward portion of one diameter and a forward portion of increased diameter toward and at said forward end; a plunger in said bore and reciprocable therein; a slider in said bore rearwardly of said plunger and reciprocable therein; seal means on said plunger and slider for sealing the same with said bore rearward portion; means for reciprocating said plunger and slider in said bore to move the same forwardly to positions whereat said plunger moves completely out of said rearward and into said forward portion of said bore and extends only partially through said forward end into the vessel and said slider is completely in said rearward portion and spaced from said forward portion of said bore and from said plunger to establish a sample chamber therebetween for reception of product flowing from the vessel and around said plunger in said increased diameter bore forward portion, and to then move said plunger and slider rearwardly into said bore rearward portion to capture the product in said sample chamber until said sample chamber is at a point in said bore rearward portion; means at said point in said bore rearward portion for receiving said sampled product; means for resisting further rearward movement of said slider when said sample chamber is at said point in said bore rearward portion, so that continued rearward movement of said plunger then decreases the volumetric capacity of said sample chamber and forces the product therefrom for reception by said means for receiving, said seal means maintaining a liquid seal between said forward end of said bore and said point therein.

2. Apparatus as claim 1, wherein said means for receiving is a passage in said housing communicating with said bore at said point therein.

3. Apparatus as in claim 1, wherein said means for reciprocating comprises a rod in said bore and connected at a forward end with said plunger, said rod extending through said slider and said slider being sealed with and movable along said rod, stop means on said rod in said bore rearwardly of said slider for preventing movement of said slider therepast, said slider having an axial length along said bore which is less than the distance between said stop means and plunger, whereby when said slider is against said stop means said sample chamber is established around said rod between said slider and said plunger, and motor means coupled with a rearward end of said rod rearwardly of said stop means for reciprocating said rod to move said slider and plunger forwardly and rearwardly in said bore.

4. Apparatus as in claim 1, wherein said means for resisting further rearward movement of said slider includes abutment means in said bore for engaging a rearward end of said slider when a forward end thereof is substantially at said point in said bore, said slider having an axial length along said bore which is slightly less than the distance between said abutment means and said plunger when said plunger is moved to its rearwardmost position in said bore to force product from said sample chamber, whereby said plunger is not moved firmly against said slider and facing surfaces of the same are therefor unlikely to become stuck together by product.

5. Apparatus for obtaining samples of a viscous liquid product from a vessel containing the product under pressure, comprising a housing having a cylindrical bore for communication at a forward end with the interior of the vessel, said bore having an increased diameter portion toward and at said forward end; sample collecting means in said bore and reciprocable therein, said sample collecting means including a rod having a stop toward a rearward end thereof, a plunger coupled with a forward end of said rod and slidingly sealed with said bore rearwardly of said increased diameter portion thereof, and a slider receiving said rod in a passage therethrough and slidingly sealed with said rod and with said bore rearwardly of said increased diameter portion, said stop being on said rod in said bore and said slider being intermediate said plunger and stop and having a length therebetween which is less than the distance therebetween, so that when said slider engages said stop a sample chamber is established around said rod between said slider and plunger; means for reciprocating said rod to move said plunger and slider forwardly through said bore until said plunger is moved into said increased diameter portion and extends only partially through said forward end into the vessel, whereupon the pressure of product in the vessel urges said slider against said stop within said bore rearwardly of said increased diameter portion and product flows around said plunger in said increased portion of said bore and fills said sample chamber, said rod and sample chamber remaining in said bore at all times, and to then move said plunger rearwardly back into said bore, the pressure of product in the vessel moving said slider rearwardly with said plunger until said plunger seals with said bore rearwardly of said increased diameter portion and captures the product in said sample chamber, whereupon continued rearward movement of said plunger moves said slider rearwardly in said bore by means of forces exerted thereon by the product sample until said sample chamber is at a point in said bore; discharge port means at said point in said bore for receiving the product sample; and means for resisting further rearward movement of said slider when said sample chamber is at said point in said bore, so that continued rearward movement of said plunger then decreases the volumetric capacity of said sample chamber and forces the product sample through said discharge port means for collection.

6. Apparatus as in claim 5, including means for introducing a gas into said bore rearwardly of said slider at a pressure which is less than the pressure of product in the vessel, said gas forcing said slider against said plunger as the same are moved forwardly to maintain said sample chamber collapsed until said sample chamber is exposed to the pressure of the product, whereupon the pressure of the product moves said slider rearwardly against the force exerted by said gas to increase the volume of said sample chamber and aid filling of said sample chamber by aspirating product therein.

7. Apparatus as in claim 5, wherein said means for reciprocating comprises pneumatic motor means coupled with the rearward end of said rod.

8. Apparatus as in claim 5, wherein said resisting means includes first seal means slidingly sealing said slider with said bore and second seal means slidingly sealing said slider with said rod, and wherein the resistance offered by said first seal means to movement of said slider through said bore is greater than the resistance offered by said second seal means to movement of said slider along said rod.

9. Apparatus as in claim 8, further including abutment means in said bore positioned to be closely spaced from the rearward end of said slider when said sample chamber is at said point in said bore, said abutment means absolutely inhibiting further rearward movement of said slider in the event said resisting means fails to terminate such movement said slider having an axial length along said bore which is slightly less than the distance between said abutment means and said plunger when said plunger is moved to its rearwardmost position in said bore to force product from said sample chamber, whereby said plunger is not moved firmly against said slider and facing surfaces of the same are therefor unlikely to become stuck together by sampled product.

10. Apparatus for obtaining samples of a liquid product from a vessel containing the product, comprising a housing having a cylindrical bore for communication at a forward end with the interior of the vessel and a discharge portion in said bore, said bore having an increased diameter portion toward and at said forward end; a plunger in and slidingly sealed with said bore rearwardly of said plunger and said increased diameter portion; a slider in and slidingly sealed with said bore rearwardly of said plunger and said increased diameter portion; means for reciprocating said plunger and slider in said bore to move the same forwardly to positions whereat said plunger is moved into said increased diameter portion and extends only partially through said forward end into the vessel and said slider is in said bore rearwardly of said increased diameter portion and spaced rearwardly from said plunger to establish a sample chamber between the same for reception of liquid product flowing from the vessel and around said plunger in said increased diameter portion and into said sample chamber, and to then move said plunger and slider rearwardly to capture the sampled product between the same within said bore rearwardly of said increased diameter portion and to convey the sample to said discharge port; a means for arresting further rearward movement of said slider when the product sample is at said discharge portion, so that continued rearward movement of said plunger then decreases the volumetric capacity of said sample chamber and forces the liquid product sample from said sample chamber and through said discharge port for collection.

11. Apparatus for obtaining samples of a liquid product from a vessel containing the product, comprising a housing having a cylindrical bore for commumincation at a forward end with the interior of the vessel and a discharge port in said bore, said bore having an increased diameter portion toward and at said forward end; a plunger in and slidingly sealed with said bore rearwardly of said increased diameter portion; a slider in and slidingly sealed with said bore rearwardly of said plunger and said increased diameter portion; means for reciprocating said plunger and slider in said bore to move the same forwardly to positions whereat said plunger is moved into said increased diameter portion and extends only partially through said forward end into the vessel and said slider is in said bore rearwardly of said increased diameter portion and spaced rearwardly from said plunger to establish a sample chamber between the same for reception of liquid product flowing from the vessel and around said plunger in said increased diameter portion and into said sample chamber, and to then move said plunger and slider rearwardly to capture the sampled product between the same in said sample chamber and within said bore rearwardly of said increased diameter portion and to convey the sample to said discharge port, said means for reciprocating, when said sample is at said discharge port, moving said slider and plunger relative to each other and together to decrease the volumetric capacity of said sample chamber and force the liquid product sample from said sample chamber and through said discharge port for collection.

* * * * *